US012629087B2

(12) United States Patent
Kim et al.

(10) Patent No.: US 12,629,087 B2
(45) Date of Patent: May 19, 2026

(54) METHOD AND APPARATUS FOR SUPPORTING PREDICTION OF NEURODEVELOPMENTAL DISORDER USING FUNDUS IMAGE

(71) Applicants: Beom Kim, Seongnam-si (KR); Hwan Kim, Seoul (KR)

(72) Inventors: Beom Kim, Seongnam-si (KR); Hwan Kim, Seoul (KR)

(73) Assignee: XAIMED CO., LTD, Seoul (KR)

( * ) Notice: Subject to any disclaimer, the term of this patent is extended or adjusted under 35 U.S.C. 154(b) by 288 days.

(21) Appl. No.: 18/429,631

(22) Filed: Feb. 1, 2024

(65) Prior Publication Data

US 2025/0248643 A1 Aug. 7, 2025

(51) Int. Cl.
*A61B 5/00* (2006.01)
*G16H 30/40* (2018.01)
*G16H 50/20* (2018.01)
*G16H 50/70* (2018.01)

(52) U.S. Cl.
CPC .......... *A61B 5/4088* (2013.01); *A61B 5/7267* (2013.01); *A61B 5/742* (2013.01); *G16H 30/40* (2018.01); *G16H 50/20* (2018.01); *G16H 50/70* (2018.01)

(58) Field of Classification Search
CPC ..... A61B 5/4088; A61B 5/7267; A61B 5/742; G16H 50/70; G16H 50/20; G16H 30/40
See application file for complete search history.

(56) References Cited

U.S. PATENT DOCUMENTS

2025/0054134 A1* 2/2025 Far ......................... G16H 30/40
2025/0099017 A1* 3/2025 Koronyo ............ A61B 5/02007

OTHER PUBLICATIONS

Kim, J. H., Hong, J., Choi, H., Kang, H. G., Yoon, S., Hwang, J. Y., . . . & Cheon, K. A. (2023). Development of deep ensembles to screen for autism and symptom severity using retinal photographs. JAMA Network Open, 6(12), e2347692-e2347692. (Year: 2023).*
Lai, M., Lee, J., Chiu, S., Charm, J., So, W. Y., Yuen, F. P., . . . & Zee, B. (2020). A machine learning approach for retinal images analysis as an objective screening method for children with autism spectrum disorder. EClinicalMedicine, 28. (Year: 2020).*

* cited by examiner

*Primary Examiner* — David Perlman
(74) *Attorney, Agent, or Firm* — Han's Law Office

(57) ABSTRACT

Provided are apparatuses, a non-transitory computer-readable medium or media, for predicting of neurodevelopmental disorder using a fundus image of a subject. In certain aspects, disclosed a method including the steps of: receiving the fundus image; processing the fundus image to classify one or more features contained in the fundus image using a machine learning model; and predicting, based on a classification, whether the fundus image is indicative of presence of neurodevelopmental disorder in the subject, wherein the machine learning model has been trained on stored fundus images obtained from at least two group of subjects who have previously been diagnosed as having the neurodevelopmental disorder, the machine learning model is trained by processes comprising; extracting a first embedding vector and a second embedding vector from a first fundus image and a second fundus image, respectively; and maximizing a similarity between the first embedding vector and the second embedding vector.

10 Claims, 14 Drawing Sheets

$$S_{i,j} = \frac{z_i^k \circ z_j^k}{|z_i^k| \times |z_j^k|}$$

Cosine similarity function

Embedding vectors

Toddlers (0-7)  Children (7-13)  Teenagers (13-21)

Normal  ADHD  ASD

Table 1. Performance comparison (ADHD classification)

| | Accuracy | Recall | Precision | F1-Score |
|---|---|---|---|---|
| VGG19 (Simonyan et al. 2014) | 0.8695 (±0.0007) | 0.8407 (±0.0008) | 0.7122 (±0.0011) | 0.7676 (±0.0008) |
| MobileNetV2 (Sandler et al. 2018) | 0.8723 (±0.0005) | 0.8578 (±0.0014) | 0.7085 (±0.0005) | 0.7762 (±0.0011) |
| EfficientNet-B7 (Tan et al. 2019) | 0.8806 (±0.0011) | 0.8662 (±0.0007) | 0.7194 (±0.0007) | 0.7804 (±0.0014) |
| HRNet-32 (Wang et al. 2020) | 0.9023 (±0.0012) | 0.8785 (±0.0007) | 0.7487 (±0.0006) | 0.7985 (±0.0008) |
| Resnet-50 (He et al. 2016) | 0.9084 (±0.0009) | 0.8874 (±0.0008) | 0.7542 (±0.0011) | 0.8095 (±0.0012) |
| Proposed Method (Resnet-50 based) | 0.9452 (±0.0008) | 0.9200 (±0.0010) | 0.7795 (±0.0001) | 0.8439 (±0.0008) |

FIG. 7

Table 2. Performance comparison (ASD classification)

| | Accuracy | Recall | Precision | F1-Score |
|---|---|---|---|---|
| VGG19 | 0.8983 (±0.0011) | 0.8333 (±0.0013) | 0.6629 (±0.0009) | 0.7308 (±0.0010) |
| MobileNetV2 | 0.9062 (±0.0009) | 0.8311 (±0.0011) | 0.6655 (±0.0010) | 0.7407 (±0.0009) |
| EfficientNet-b7 | 0.9183 (±0.0014) | 0.8427 (±0.0011) | 0.6727 (±0.0013) | 0.7486 (±0.0008) |
| HRNet-32 | 0.9208 (±0.0016) | 0.8554 (±0.0008) | 0.6896 (±0.0009) | 0.7545 (±0.0010) |
| Resnet-50 | 0.9367 (±0.0007) | 0.8522 (±0.0011) | 0.6838 (±0.0009) | 0.7584 (±0.0016) |
| Proposed Method (Resnet-50 based) | 0.9754 (±0.0010) | 0.9004 (±0.0011) | 0.7325 (±0.0009) | 0.8077 (±0.0012) |

FIG. 9

Table 3. Data augmentation result

| | Accuracy (ADHD) | Accuracy (ASD) |
|---|---|---|
| Baseline | 0.9452 (±0.0008) | 0.9754 (±0.0010) |
| Grayscale | 0.9075 (±0.0007) | 0.9471 (±0.0008) |
| YCbCr | 0.9253 (±0.0011) | 0.9623 (±0.0009) |
| Sharpness | 0.9187 (±0.0013) | 0.9575 (±0.0011) |
| Histogram Equalization | 0.9589 (±0.0009) | 0.9862 (±0.0007) |

FIG. 11

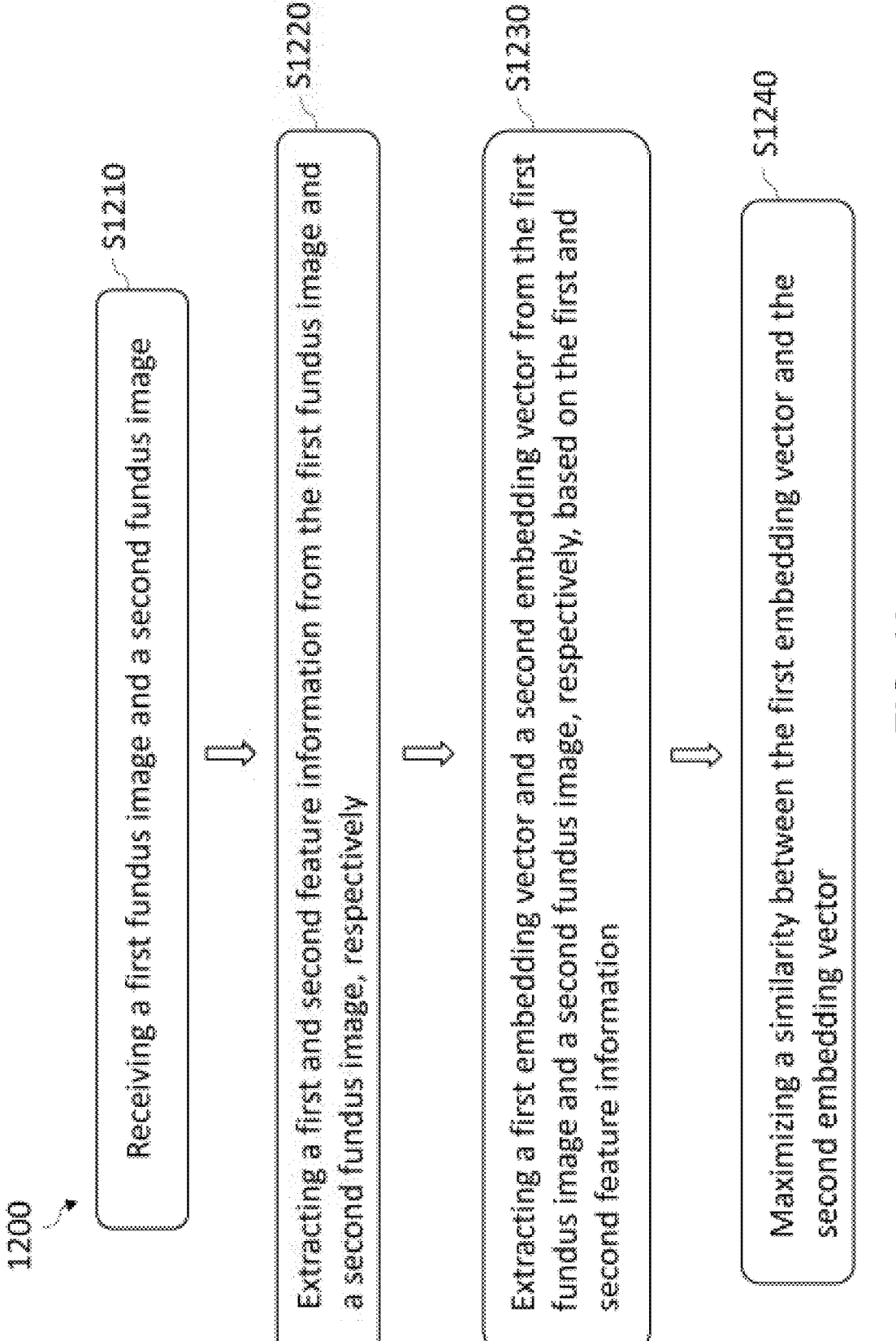

1200

S1210

Receiving a first fundus image and a second fundus image

S1220

Extracting a first and second feature information from the first fundus image and a second fundus image, respectively

S1230

Extracting a first embedding vector and a second embedding vector from the first fundus image and a second fundus image, respectively, based on the first and second feature information

S1240

Maximizing a similarity between the first embedding vector and the second embedding vector

FIG. 12

METHOD AND APPARATUS FOR SUPPORTING PREDICTION OF NEURODEVELOPMENTAL DISORDER USING FUNDUS IMAGE

A. TECHNICAL FIELD

The present disclosure relates to predicting neurodevelopmental disorder using a biometric image, more particularly, to an apparatus and method for supporting prediction of the neurodevelopmental disorder using a fundus image based on a machine learning model.

B. DESCRIPTION OF THE RELATED ART

With development of artificial intelligence learning models, many machine learning models are being used to read medical images. In a fundus image of the medical images, the machine learning models are currently being used to support an image reading, an image finding, an image diagnosis to predict a disease of a patient. More specifically, a method of supporting the image reading, the image finding, the image diagnosis of the fundus image is to obtain the fundus image from the patient, extract feature from the fundus image based on the machined learning models, provide the feature to a practitioner, and predict the patient's disease based on it. In this case, the feature includes various information for the fundus image.

Meanwhile, neurodevelopmental disorders like autism spectrum disorder (ASD) and attention-deficit/hyperactivity disorder (ADHD) pose substantial challenges to the cognitive, social, and emotional development of children. Early and precise diagnosis of autism spectrum disorder and attention-deficit/hyperactivity disorder holds significant importance in facilitating timely interventions and support, ultimately enhancing outcomes for individuals affected by these conditions. Conventional diagnostic approaches for these disorders have traditionally depended on behavioral assessments, clinical observations, and structured interviews. While these methods are valuable and provide accurate results, they are labor-intensive, time-consuming, and subject to variations in judgments. As a result, there is a growing need for more efficient and objective diagnostic approaches.

SUMMARY OF THE DISCLOSURE

In one aspect of the present disclosure, an apparatus for predicting of neurodevelopmental disorder using a fundus image of a subject includes a processor; and a memory comprising one or more sequences of instructions which, when executed by the processor, causes steps to be performed comprising receiving the fundus image, processing the fundus image to classify one or more features contained in the fundus image using a machine learning model and predicting, based on a classification, whether the fundus image is indicative of presence of neurodevelopmental disorder in the subject, wherein the machine learning model has been trained on stored fundus images obtained from at least two group of subjects who have previously been diagnosed as having the neurodevelopmental disorder, the machine learning model is trained by a process including extracting a first embedding vector and a second embedding vector from a first fundus image and a second fundus image, respectively and maximizing a similarity between the first embedding vector and the second embedding vector.

Desirably, the processes further may comprise extracting a first feature information and a second feature information from the first fundus image and the second fundus image, respectively.

Desirably, the first feature information and the second feature information may include at least one of retinal vessel information and optic nerve change information in the fundus image.

Desirably, the similarity may be calculated with a cosine similarity function.

Desirably, the first fundus image and the second fundus image may be images diagnosed as having autism spectrum disorder or attention-deficit/hyperactivity disorder.

In another aspect of the present disclosure, an apparatus for predicting of neurodevelopmental disorder using a fundus image of a subject includes a processor; and a memory comprising one or more sequences of instructions which, when executed by the processor, causes steps to be performed comprising receiving the fundus image, processing the fundus image to classify one or more features contained in the fundus image using a machine learning model and predicting, based on a classification, whether the fundus image is indicative of presence of neurodevelopmental disorder in the subject, wherein the machine learning model has been trained on stored fundus images obtained from at least two group of subjects who have previously been diagnosed as having the neurodevelopmental disorder, the machine learning model is trained by a process including extracting a first feature information and a second feature information from a first fundus image and a second fundus image, respectively; extracting a first embedding vector and a second embedding vector from the first fundus image and the second fundus image, respectively, based on the first feature information and the second feature information; and maximizing a similarity between the first embedding vector and the second embedding vector.

BRIEF DESCRIPTION OF THE DRAWINGS

References will be made to embodiments of the disclosure, examples of which may be illustrated in the accompanying figures. These figures are intended to be illustrative, not limiting. Although the disclosure is generally described in the context of these embodiments, it should be understood that it is not intended to limit the scope of the disclosure to these particular embodiments.

FIG. 7 shows a table of performance comparison of overall attention-deficit/hyperactivity disorder (ADHD) classification results achieved by the computing device shown in FIG. 1 based on comparison with state-of the-art methods according to embodiments of the present disclosure.

FIG. 9 shows a table of performance comparison of overall autism spectrum disorder (ASD) classification results achieved by the computing device shown in FIG. 1 based on comparison with state-of the-art methods according to embodiments of the present disclosure.

FIG. 11 shows a table of data augmentation experiment achieved by the machine learning model according to embodiments of the present disclosure.

FIG. 12 is an exemplary flow diagram showing a training process of a machine learning model according to embodiments of present disclosure.

DETAILED DESCRIPTION OF PREFERRED EMBODIMENTS

Figure 1:
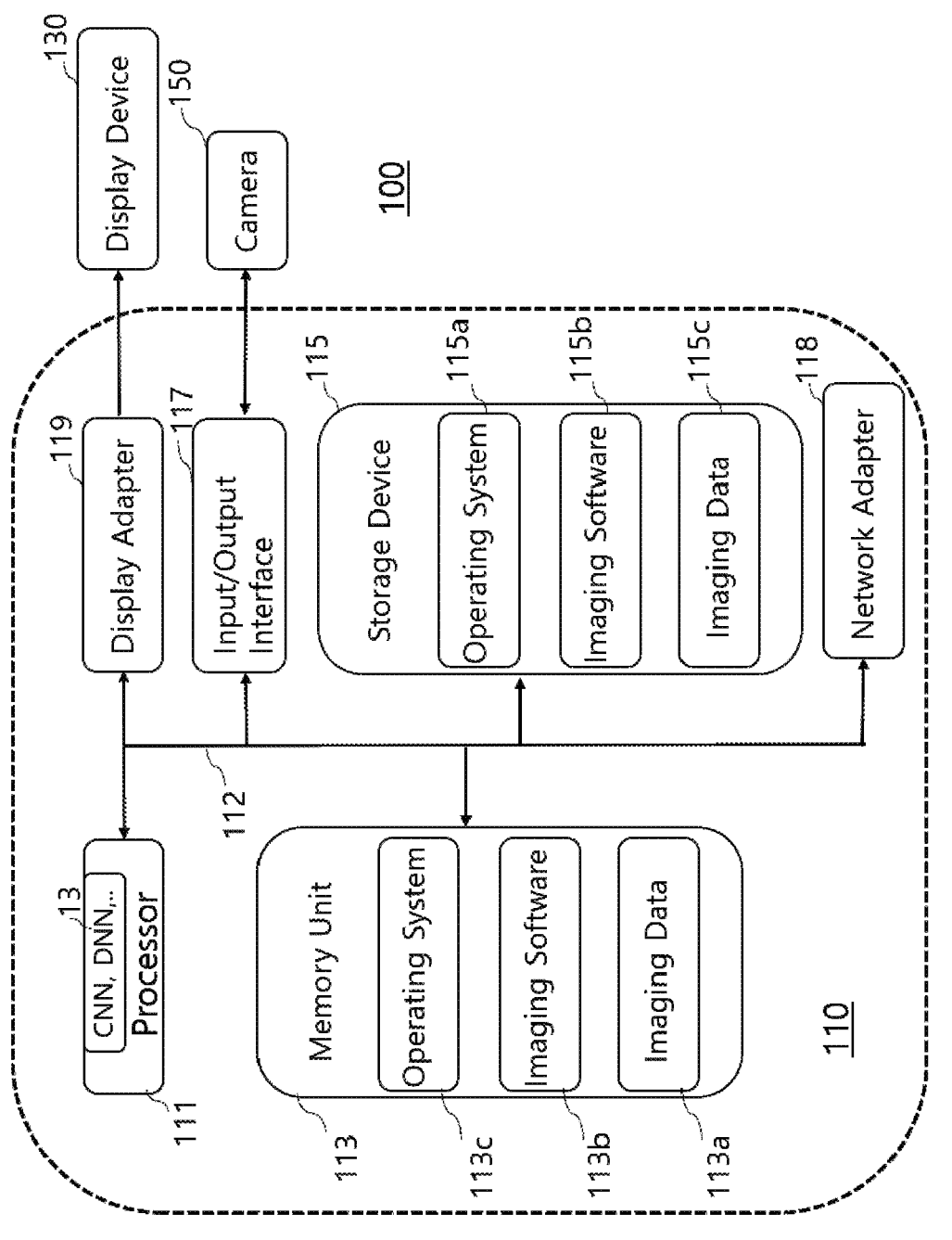
FIG. 1 is a schematic diagram of an illustrative apparatus for supporting predicting of neurodevelopmental disorder disease using a fundus image according to embodiments of the present disclosure.

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, a device, or a method on a tangible computer-readable medium.

Components shown in diagrams are illustrative of exemplary embodiments of the disclosure and are meant to avoid obscuring the disclosure. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components that may be implemented in software, hardware, or a combination thereof.

It shall also be noted that the terms "coupled," "connected," "linked," or "communicatively coupled" shall be understood to include direct connections, indirect connections through one or more intermediary devices, and wireless connections.

Furthermore, one skilled in the art shall recognize: (1) that certain steps may optionally be performed; (2) that steps may not be limited to the specific order set forth herein; and (3) that certain steps may be performed in different orders, including being done contemporaneously.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments.

In the following description, it shall also be noted that the terms "learning" shall be understood not to intend mental action such as human educational activity because of referring to performing machine learning by a processing module such as a processor, a CPU, an application processor, micro-controller, so on.

An "image" is defined as a reproduction or imitation of the form of a person or thing, or specific characteristics thereof, in digital form. An image can be, but is not limited to, a JPEG image, a PNG image, a GIF image, a TIFF image, or any other digital image format known in the art. "Image" is used interchangeably with "photograph".

A "feature(s)" or "feature information" is defined as a group of one or more descriptive characteristics of subjects that can discriminate for disease. A feature can be a numeric attribute.

The terms "comprise/include" used throughout the description and the claims and modifications thereof are not intended to exclude other technical features, additions, components, or operations.

The terminology used herein is for purposes of describing particular embodiments only and is not intended to be limiting. The defined terms are in addition to the technical and scientific meanings of the defined terms as commonly understood and accepted in the technical field of the present teachings.

Relative terms may be used to describe the various elements' relationships to one another, as illustrated in the accompanying drawings. These relative terms are intended to encompass different orientations of the device and/or elements in addition to the orientation depicted in the drawings.

Unless the context clearly indicates otherwise, the singular forms "a," "an," and "the" are intended to include the plural forms as well. Also, when description related to a known configuration or function is deemed to render the present disclosure ambiguous, the corresponding description is omitted.

FIG. 1 is a schematic diagram of an illustrative apparatus 100 for supporting predicting of neurodevelopmental disorder disease using a fundus image according to embodiments of the present disclosure.

As depicted, the apparatus 100 may include a computing device 110, a display device 130 and a camera 150. In embodiments, the computing device 110 may include, but is not limited thereto, one or more processor 111, a memory unit 113, a storage device 115, an input/output interface 117, a network adapter 118, a display adapter 119, and a system bus 112 connecting various system components to the memory unit 113. In embodiments, the apparatus 100 may further include communication mechanisms as well as the system bus 112 for transferring information. In embodiments, the communication mechanisms or the system bus 112 may interconnect the processor 111, a computer-readable medium, a short range communication module (e.g., a Bluetooth, a NFC), the network adapter 118 including a network interface or mobile communication module, the display device 130 (e.g., a CRT, a LCD, etc.), an input device (e.g., a keyboard, a keypad, a virtual keyboard, a mouse, a trackball, a stylus, a touch sensing means, etc.) and/or subsystems. In embodiments, the camera 150 may include an image sensor (not shown) that captures an image of an subject and photoelectrically converts the image into an image signal, and may photograph a fundus image of the subject using the image sensor. The photographed fundus image may be stored in the memory unit 113 or the storage device 115, or may be provided to the processor 111 through the input/output interface 117 and processed based on the machine learning model 13.

In embodiments, the processor 111 is configured to perform one or more machine learning models 13, which can be implemented in hardware, software, firmware, or a combination thereof. The processor 111 may be, but is not limited to, a processing module, a Computer Processing Unit (CPU), an Application Processor (AP), a microcontroller, a digital signal processor. In embodiments, the processor 111 may include an image filter such as a high pass filter or a low pass filter to filter a specific factor in a fundus image. In addition, in embodiments, the processor 111 may communicate with a hardware controller such as the display adapter 119 to display a user interface on the display device 130. In embodiments, the processor 111 may access the memory unit 113 and execute commands stored in the memory unit 113 or one or more sequences of instructions to control the operation of the apparatus 100. The commands or sequences of instructions may be read in the memory unit 113 from computer-readable medium or media such as a static storage or a disk drive, but is not limited thereto. In alternative embodiments, a hard-wired circuitry which is equipped with a hardware in combination with software commands may be used. The hard-wired circuitry can replace the soft commands. The instructions may be an arbitrary medium for providing the commands to the processor 111 and may be loaded into the memory unit 113.

In embodiments, the system bus 112 may represent one or more of several possible types of bus structures, including a memory bus or memory controller, a peripheral bus, an accelerated graphics port, and a processor or local bus using any of a variety of bus architectures. For instance, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. In embodiments, the system bus 112, and all buses specified in this description can also be implemented over a wired or wireless network connection.

A transmission media including wires of the system bus 112 may include at least one of coaxial cables, copper wires, and optical fibers. For instance, the transmission media may take a form of sound waves or light waves generated during radio wave communication or infrared data communication.

In embodiments, the apparatus 100 may transmit or receive the commands including messages, data, and one or more programs, i.e., a program code, through a network link or the network adapter 118. In embodiments, the network adapter 118 may include a separate or integrated antenna for enabling transmission and reception through the network link. The network adapter 118 may access a network and communicate with a remote computing devices 200, 300, 400 in FIG. 2.

In embodiments, the network may be, but is not limited to, at least one of LAN, WLAN, PSTN, and cellular phone networks. The network adapter 118 may include at least one of a network interface and a mobile communication module for accessing the network. In embodiments, the mobile communication module may be accessed to a mobile communication network for each generation such as 2G to 5G mobile communication network.

In embodiments, on receiving a program code, the program code may be executed by the processor 111 and may be stored in a disk drive of the memory unit 113 or in a non-volatile memory of a different type from the disk drive for executing the program code.

In embodiments, the computing device 110 may include a variety of computer-readable medium or media. The computer-readable medium or media may be any available medium or media that are accessible by the computing device 100. For example, the computer-readable medium or media may include, but is not limited to, both volatile and non-volatile media, removable or non-removable media.

In embodiments, the memory unit 113 may typically stores a database of fundus images that are used by the machine learning model 13, as described below in detail, although the database could be at some other location that is external to the remote computing devices 200, 300, 400 and accessible by the processor 111 via a network. The memory unit 113 may store a driver, an application program, data, and a database for operating the apparatus 100 therein. In addition, the memory unit 113 may include a computer-readable medium in a form of a volatile memory such as a random access memory (RAM), a non-volatile memory such as a read only memory (ROM), and a flash memory. For instance, it may be, but is not limited to, a hard disk drive, a solid state drive, an optical disk drive.

In embodiments, each of the memory unit 113 and the storage device 115 may be program modules such as the imaging software 113b, 115b and the operating systems 113c, 115c that can be immediately accessed so that a data such as the imaging data 113a, 115a is operated by the processor 111.

In embodiments, the machine learning model 13 may be trained to classify retinal features contained in fundus images and to predict, based on the classification, the presence of neurodevelopmental disorder disease in a human subject. The manner in which training may be performed and the manner in which the apparatus 100 is used to predict the presence of the neurodevelopmental disorder disease in a human subject are described below. Once trained, the machine learning model 13 may analyze fundus images captured by the image acquisition device like a camera 150 to identify and classify retinal features contained in the images. Based on the classification of the retinal features, the machine learning model 13 may predicts the presence of neurodevelopmental disorder disease such as autism spectrum disorder (ASD) and attention-deficit/hyperactivity disorder (ADHD) in human subject. In embodiments, the machine learning model 13 may be installed into at least one of the processor 111, the memory unit 113 and the storage device 115. The machine learning model 13 may use, but is not limited to, at least one of a deep neural network (DNN), a convolutional neural network (CNN) and a recurrent neural network (RNN), which are one of the machine learning algorithms.

Figure 2:
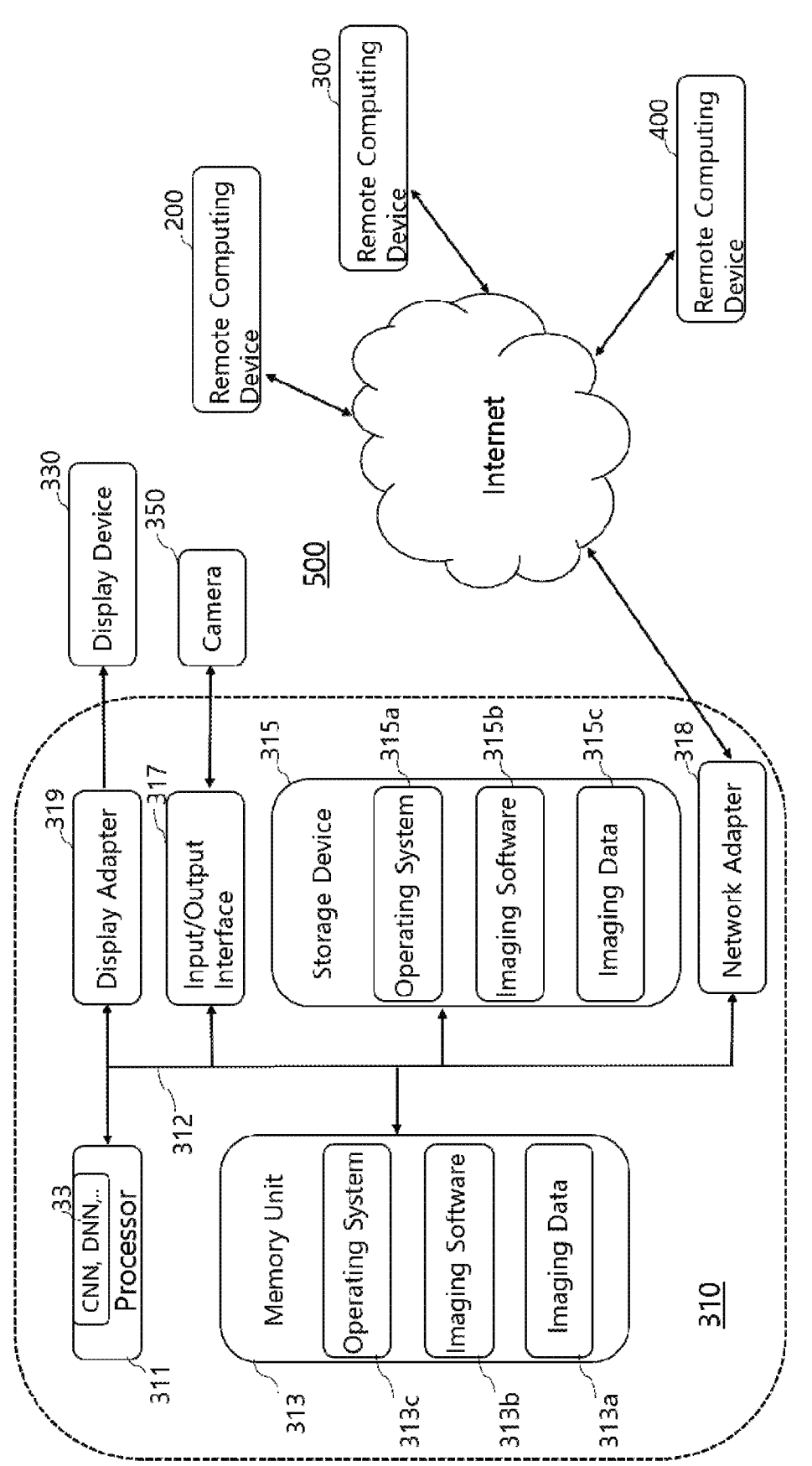
FIG. 2 is a schematic diagram of an illustrative system for supporting predicting of neurodevelopmental disorder disease using a fundus image according to embodiments of the present disclosure.

FIG. 2 is a schematic diagram of an illustrative system 500 for supporting predicting of neurodevelopmental disorder disease using a fundus image according to embodiments of the present disclosure.

As depicted, the system 500 may include a computing device 310 and one and more remote computing devices 200, 300, 400. In embodiments, the computing device 310 and the remote computing devices 200, 300, 400 may be connected to each other through a network. The components 310, 311, 312, 313, 315, 317, 318, 319, 330 of the system 500 are similar to their counterparts in FIG. 2. In embodiments, each of remote computing devices 200, 300, 400 may be similar to the apparatus 100 in FIG. 1. For instance, each of remote computing devices 200, 300, 400 may include each of the subsystems, including the processor 311, the memory unit 313, an operating system 313c, 315a, an imaging software 313b, 315b, an imaging data 313a, 315c, a network adapter 318, a storage device 315, an input/output interface 317 and a display adapter 319. Each of remote computing devices 200, 300, 400 may further include a display device 330 and a camera 350. In embodiments, the system bus 312 may connect the subsystems to each other.

In embodiments, the computing device 310 and the remote computing devices 200, 300, 400 may be configured to perform one or more of the methods, functions, and/or operations presented herein. Computing devices that implement at least one or more of the methods, functions, and/or operations described herein may comprise an application or applications operating on at least one computing device. The computing device may comprise one or more computers and one or more databases. The computing device may be a single device, a distributed device, a cloud-based computer, or a combination thereof.

It shall be noted that the present disclosure may be implemented in any instruction-execution/computing device or system capable of processing data, including, without limitation laptop computers, desktop computers, and servers. The present disclosure may also be implemented into other computing devices and systems. Furthermore, aspects of the present disclosure may be implemented in a wide variety of ways including software (including firmware), hardware, or combinations thereof. For example, the functions to practice various aspects of the present disclosure may be performed by components that are implemented in a wide variety of ways including discrete logic components, one or more application specific integrated circuits (ASICs), and/or program-controlled processors. It shall be noted that the manner in which these items are implemented is not critical to the present disclosure.

Figure 3A:
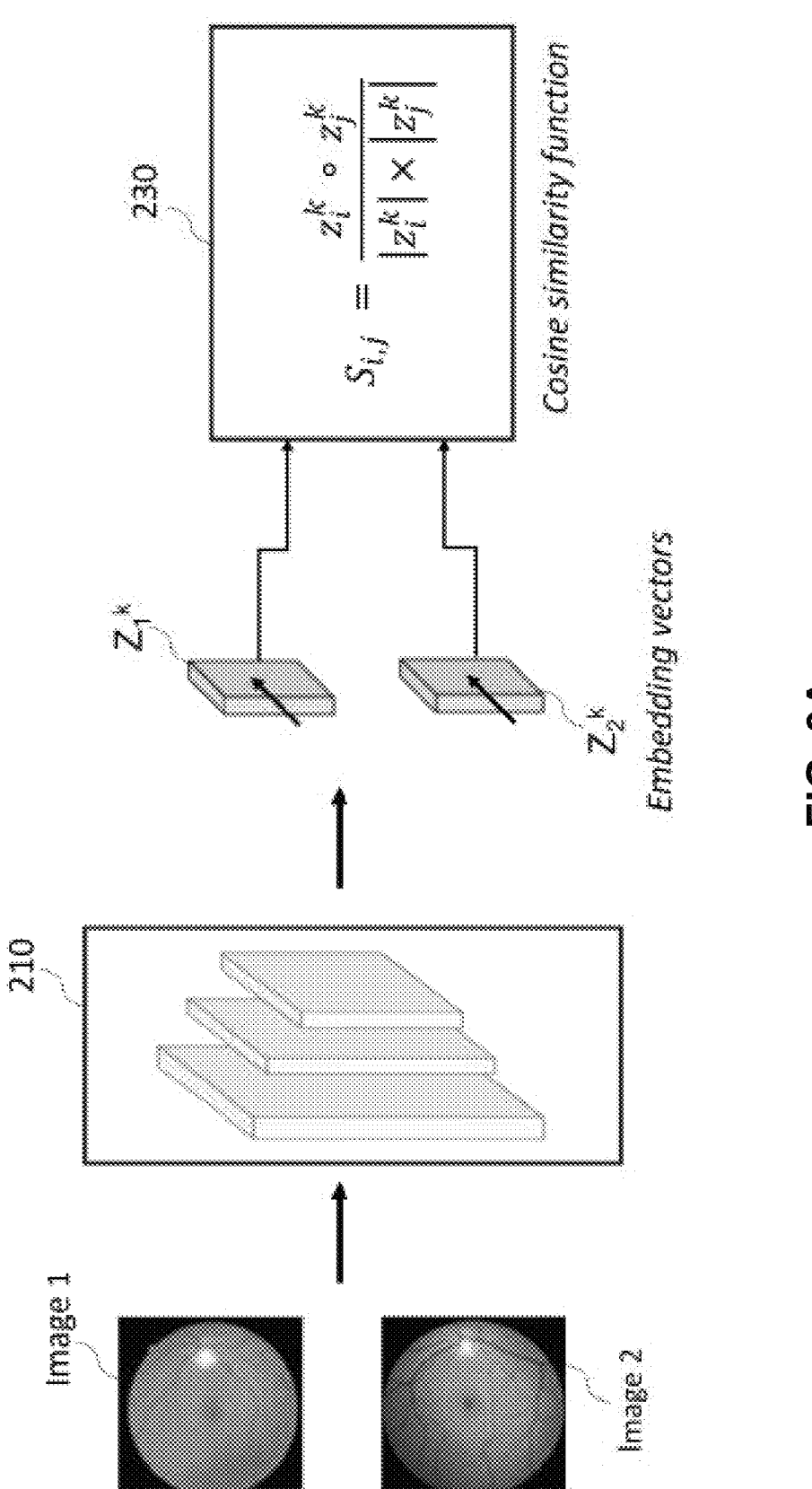
FIG. 3A is an exemplary diagram of a first architecture of a machine learning model for learning a process according to embodiments of the present disclosure.

FIG. 3A is an exemplary diagram of a first architecture of a machine learning model for learning a process according to embodiments of the present disclosure.

As depicted, in embodiments, a machine learning model 210 may extract a first embedding vector $Z_1^{\ k}$ and a second embedding vector $Z_2^{\ k}$ from the input first and second fundus images Image$_1$, Image$_2$, respectively. Each embedding vector may capture meaningful characteristics inherent to the input fundus images. In embodiments, the machine learning model 210 may process the first and second fundus images Image$_1$, Image$_2$ to maximize a mathematical similarity between the first embedding vector $Z_1^{\ k}$ and the second embedding vector $Z_2^{\ k}$ extracted from the first and second fundus images Image$_1$, Image$_2$ having the neurodevelopmental disorder disease of the same category. In this case, a similarity measurer 230 may measure the mathematical similarity between the first and second embedding vectors $Z_1^{\ k}$, $Z_2^{\ k}$ using a cosine similarity function. The similarity score may be calculated by the following cosine similarity function as shown in Equation 1.

$$\text{Cosine Similarity Function} \qquad \text{Equation 1}$$

$$S_{i,j} = \frac{z_i^k \circ z_j^k}{|z_i^k| \times |z_j^k|}$$

In the Equation 1, $S_{i,j}$ denotes the similarity score between embedding vectors $Z_i$ and $Z_j$. The operation represents the dot product. If the two input vectors have identical directions, the similarity score becomes 1, otherwise, if the directions are opposite, the similarity score becomes $-1$. Given this characteristic, it can utilize these calculated similarities as scores for implementing a classification training approach.

In embodiments, the input first and second fundus images Image$_1$, Image$_2$ may be images diagnosed as having the neurodevelopmental disorder of a same category. For example, the category may be autism spectrum disorder (ASD) and attention-deficit/hyperactivity disorder (ADHD).

A result of the extracted embedding vector $Z_1^{\ k}$, $Z_2^{\ k}$ may be stored in a memory unit 113 or a storage device 115 described above. In embodiments, the machine learning model 210 may be installed into a processor 111 and executed by the processor 111 in FIG. 1. The machine learning model 210 may be installed into a computer-readable medium or media (not shown in FIG. 1) and executed by the computer-readable medium or media. In alternative embodiments, the machine learning model 210 may be installed into the memory unit 113 or the storage device 115 and executed by the processor 111.

In addition, clinical information of a subject (e.g., a patient) may be stored into the memory unit 113 or the storage device 115 in advance. In embodiments, the machine learning model 210 may extract the embedding vectors $Z_1^{\ k}$, $Z_2^{\ k}$ of the first and second fundus images Image$_1$, Image$_2$ using the clinical information of the subject. In embodiments, the clinical information may be, but is not limited to, the age, sex, medical history, questionnaire information, test measurement values, exercise habits, eating habits, family history related to the medical history, alcohol consumption, smoking status. In embodiments, the questionnaire information may include neuromedical questionnaire that a practitioner (e.g., a medical doctor) can perform on the subject or may mean ideal findings currently observed to the subject, unlike medical history thereof.

Meanwhile, a softmax function may be applied to each similarity score denoted in Equation 1 to compute a probability of the similarity score $S_{i,j}$. For example, the softmax function is as follows.

$$\text{Softmax Function} \qquad \text{Equation 2}$$

$$P_{i,j} = \frac{e^{S_{i,j}}}{\sum_{m=1}^{M} e^{S_{i,m}}}$$

In the equation 2, $P_{i,j}$ denotes the probability of similarity score $S_{i,j}$. The probability may be normalized into a numerical value between 0 and 1. Also, the converted probability may be used to measure an error using a cross-entropy loss function. The error may be the difference between the probabilities of similarity score and the true labels of a given dataset. The cross-entropy loss function may be calculated as follows.

$$\text{Cross-entropy Loss Function (loss of similarity)} \qquad \text{Equation 3}$$
$$L_{cross-entropy-similarity} = -\log_e P_{i,j}$$

According to the cross-entropy loss function of equation 3, when the similarity score $S_{i,j}$ is maximized, the probability $P_{i,j}$ approaches 1, resulting in a loss value of 0. Conversely, if the similarity score $S_{i,j}$ is minimized, the probability $P_{i,j}$ approaches 0, leading to an infinite loss value. As such, the machine learning model 210 may be repeatedly trained to maximize the similarity between the first embedding vector $Z_1{}^k$ and the second embedding vector $Z_2{}^k$ extracted from the first and second fundus images Image$_1$, Image$_2$ belonging to the neurodevelopmental disorder of the same category in order to minimize the cross-entropy loss function. This training can enhance the machine learning model's generalization capabilities for the fundus images, resulting in improved classification accuracy during subsequently diagnosing the neurodevelopmental disorder.

Figure 3B:
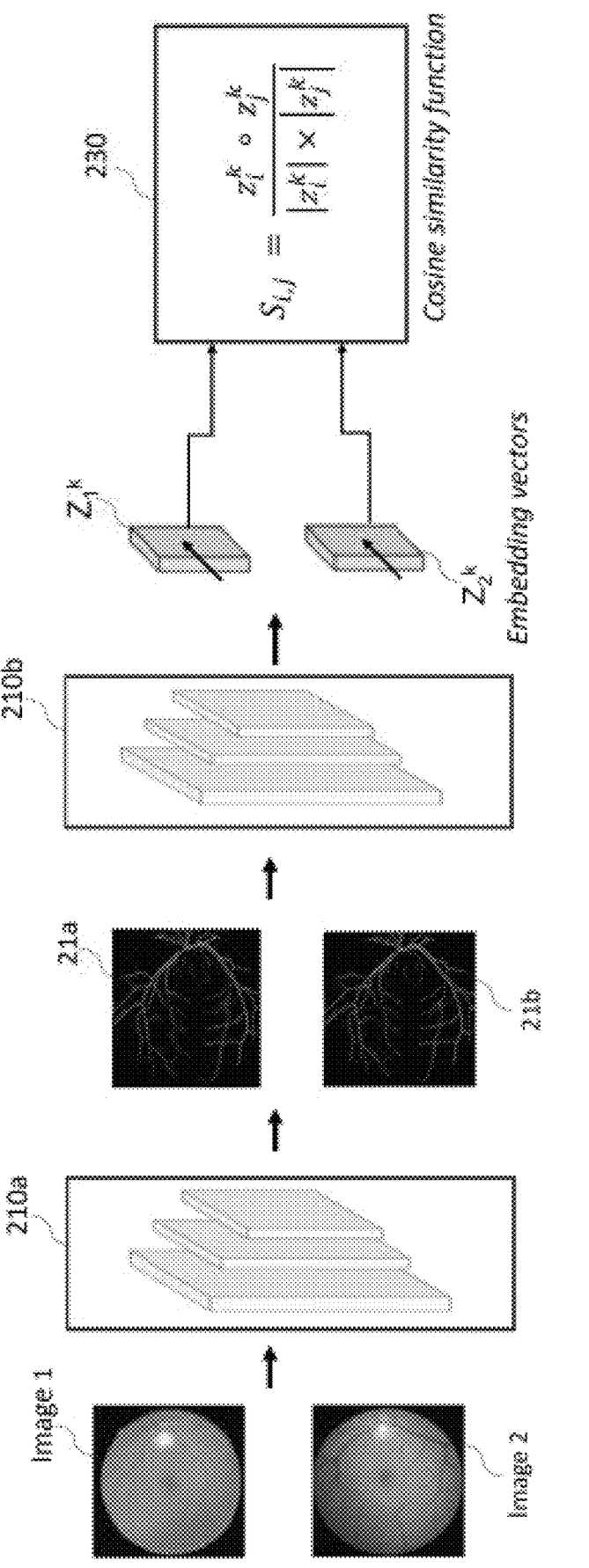
FIG. 3B is an exemplary diagram of a second architecture of a machine learning model for learning a process according to embodiments of the present disclosure.

FIG. 3B is an exemplary diagram of a second architecture of a machine learning model for learning a process according to embodiments of the present disclosure.

As depicted, in embodiments, the machine learning models 210a, 210b may comprise at least two machine learning stages, namely, a feature information extraction stage and an embedding vector extraction stage. In the feature information extraction stage, a first machine learning model 210a may extract a first and second feature information 21a, 21b from the input first and second fundus images Image$_1$, Image$_2$, respectively. The input first and second fundus images Image$_1$, Image$_2$ may be images diagnosed as having the neurodevelopmental disorder of a same category. For example, the category may be autism spectrum disorder (ASD) and attention-deficit/hyperactivity disorder (ADHD).

The extracted feature information 21a, 21b may be stored in a memory unit 113 or a storage device 115 described above. In embodiments, the machine learning models 210a, 210b may be installed into a processor 111 and executed by the processor 111 in FIG. 1. The machine learning models 210a, 210b may be installed into a computer-readable medium or media (not shown in FIG. 1) and executed by the computer-readable medium or media. In alternative embodiments, the machine learning model 210a, 210b may be installed into the memory unit 113 or the storage device 115 and executed by the processor 111.

In addition, clinical information of a subject (e.g., a patient) may be stored into the memory unit 113 or the storage device 115 in advance. In embodiments, the first machine learning model 210a may extract the feature information 21a, 21b of the first and second fundus images Image$_1$, Image$_2$ using the clinical information of the subject. In embodiments, the clinical information may be, but is not limited to, the age, sex, medical history, questionnaire information, test measurement values, exercise habits, eating habits, family history related to the medical history, alcohol consumption, smoking status. In embodiments, the questionnaire information may include neuromedical questionnaire that a practitioner (e.g., a medical doctor) can perform on the subject or may mean ideal findings currently observed to the subject, unlike medical history thereof.

In embodiments, the feature information 21a, 21b may be various information that it can support an entity (e.g., a practitioner or a computing device) reading of fundus images such as predicting or diagnosing disease. For instance, when predicting or diagnosing neurodevelopmental disorder disease in the fundus image of the subject, the feature information 21a, 21b may include at least one of various information such as a retinal vessel information, a macula information including a fovea, a cotton wool spot information and an optic nerve change information included in the fundus image. The feature information 21a, 21b may be shown in a saliency map form by a saliency map generator (not shown). The saliency may serve as a bio-marker and can be displayed on display device 130.

In the embedding vector extraction stage, a second machine learning model 210b may extract a first embedding vector $Z_1{}^k$ and a second embedding vector $Z_2{}^k$ from the input first and second fundus images Image$_1$, Image$_2$, respectively, on the basis of the feature information 21a, 21b or regardless of the feature information 21a, 21b. Each embedding vector may capture meaningful characteristics inherent to the input fundus images Image$_1$, Image$_2$. In embodiments, the machine learning model may process the first and second fundus images Image$_1$, Image$_2$ to maximize a mathematical similarity between the first embedding vector $Z_1{}^k$ and the second embedding vector $Z_2{}^k$ extracted from the first and second fundus images Image$_1$, Image$_2$ having the neurodevelopmental disorder disease of the same category. In this case, a similarity measurer may measure the mathematical similarity between the first and second embedding vectors $Z_1{}^k$, $Z_2{}^k$ using a cosine similarity function. The similarity score may be calculated by the above cosine similarity function shown in Equation 1. Also, the above softmax function and cross-entropy loss function shown in Equations 2 and 3 may be utilized to compute a probability of the similarity score Si,j and to measure an error which is the difference between the probabilities of similarity score and the true labels of a given dataset.

As such, the machine learning model 210a, 210b may be repeatedly trained to maximize the similarity between the first embedding vector $Z_1{}^k$ and the second embedding vector $Z_2{}^k$ extracted from the first and second fundus images Image$_1$, Image$_2$ belonging to the neurodevelopmental disorder of the same category in order to minimize the cross-entropy loss function.

Figure 4:
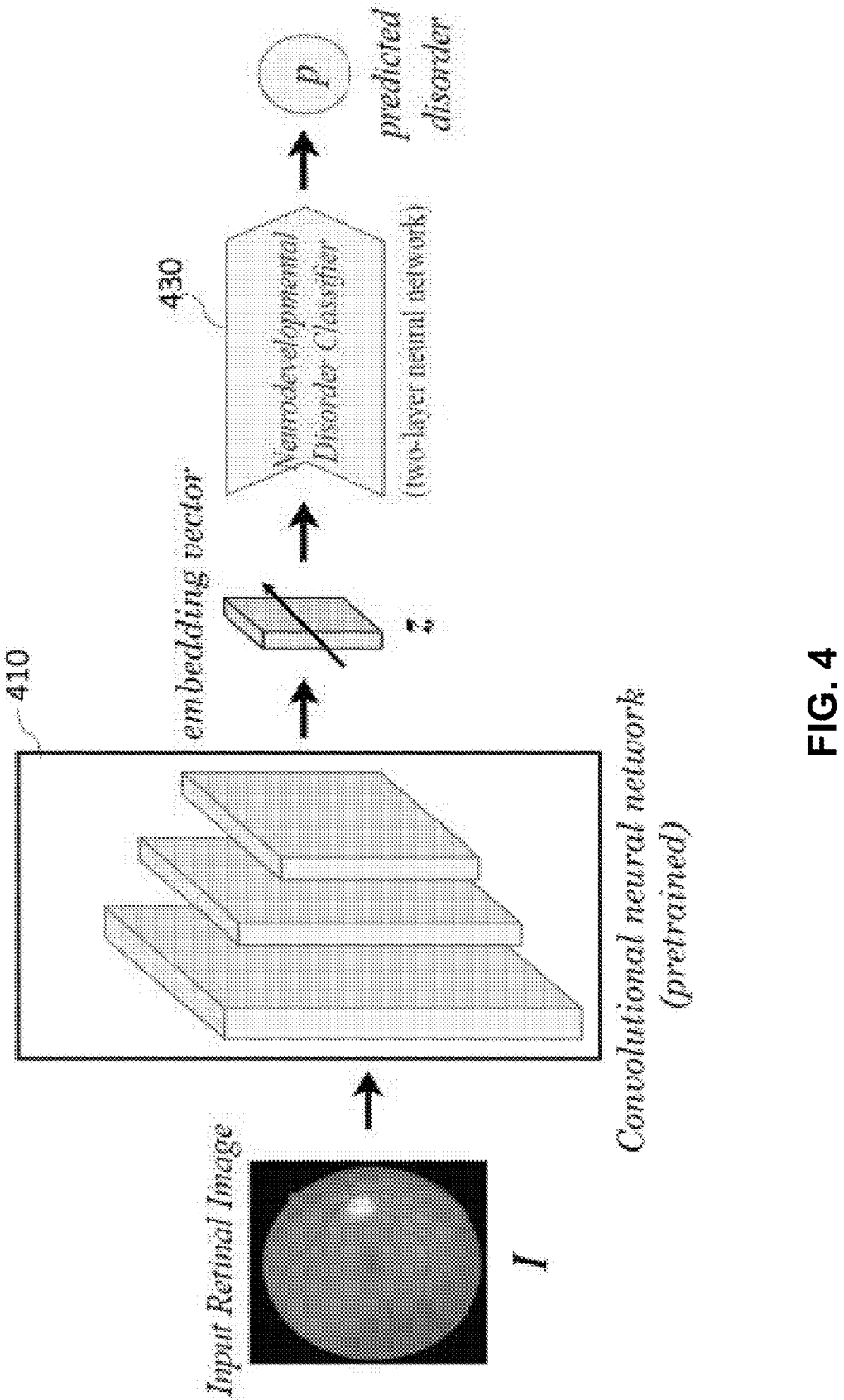
FIG. 4 is an exemplary diagram of an architecture of a machine learning model for predicting of neurodevelopmental disorder disease according to embodiments of the present disclosure.

FIG. 4 is an exemplary diagram of an architecture of a machine learning model for predicting of neurodevelopmental disorder disease according to embodiments of the present disclosure.

As depicted, if a single fundus image I is input into the machine learning model 410, the machine learning model 410 may extract an embedding vector Z from a fundus image I. The extracted embedding vector Z is subsequently passed to the neurodevelopmental disorder classifier network 430, which may predict a type of disorder presented in the inputted fundus image I. In this case, the machine learning model 410 may be a pre-trained convolutional neural network used in the previous learning stage in the FIGS. 3A and 3B and serve as the starting point for the fine-tuning process, rather than initializing random variables. This approach can accelerate the training process and enhances the accuracy of the diagnosis classification.

By the way, in embodiments, to measure the error between the predicted disorder and its ground truth, the cross-entropy loss function may be utilized for a disorder and gender classifier.

Cross−entropy Loss Function (loss of predicted disorder type) Equation 4

$$L_{cross-entropy-disorder} = -\log_e P$$

Cross−entropy Loss Function (loss of predicted gender)    Equation 5

$$L_{cross-entropy-gender} = -\log_e g$$

In the equations 4 and 5, P and g denote the probability of the predicted disorder type and gender, respectively.

Figure 5:
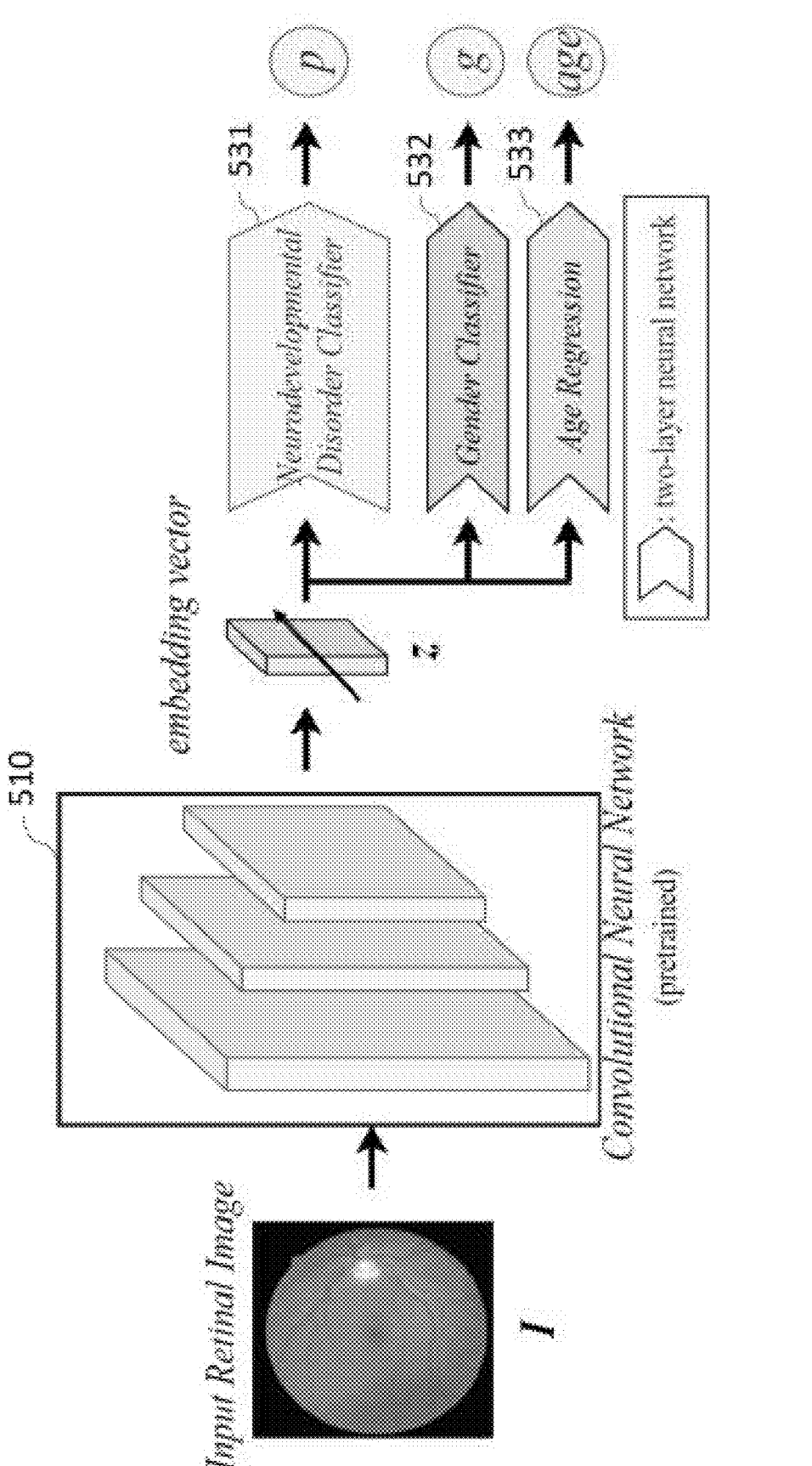
FIG. 5 is an exemplary diagram of an another architecture of a machine learning model for predicting of neurodevelopmental disorder disease according to embodiments of the present disclosure.

FIG. 5 is an exemplary diagram of an another architecture of a machine learning model for predicting of neurodevelopmental disorder disease according to embodiments of the present disclosure.

As depicted, a machine learning model 510 may be a pre-trained convolutional neural network used in the previous learning stage described in the FIGS. 3A and 3B. In embodiments, the machine learning model 510 may extract an embedding vector Z from the input fundus image I and the neurodevelopmental disorder classifier 531 may predict a type of disorder presented in the inputted fundus image I based on the embedding vector Z.

Meanwhile, Age and gender may have correlations with neurodevelopmental disorders. In embodiments, a gender classifier network 532 and an age regression network 533 may be applied to in the another architecture of the machine learning model. Accordingly, the machine learning model 510 may be jointly trained for a gender classification network 532 and an age regression network 533.

For assessing the accuracy of predicted gender and age, a cross-entropy loss function and a mean squared error function may be utilized for the gender classifier network and the age regression network, respectively. The cross-entropy loss function is similar to the Equation 4 above and the mean squared error function is as follows.

Mean Squared Error Function                Equation 6

$$L_{mean-squared-error} = \frac{1}{N}\sum_{n=1}^{N}|y - \hat{y}|$$

In equation 6, $\hat{y}$ and y represent the predicted age and its ground truth age. The variable N denotes the total number of samples. The mean squared error function may simply measure the average error between the prediction and its ground truth. Finally, the total loss function may be explained in equation 7.

Total Loss Function (fine−tuning)        Equation 7

$$L_{mean-squared-error} =$$
$$L_{cross-entropy-disorder} + \alpha\, L_{cross-entropy-gender} + \beta\, L_{mean-squared-error}$$

Here, $\alpha$ and $\beta$ are variables that assign weights for each gender classification and age regression loss. The variables may be assigned for optimal values.

For the architecture design, two-layer neural networks may be utilized for both the gender classification and age regression networks, as well as the neurodevelopmental disorder classifier. Increasing the depth of the neural network beyond two layers did not significantly contribute to improving accuracy. Therefore, it is desirable that two layer neural networks are sufficient to achieve state-of-the-art performance.

Experiments

Figure 6B:
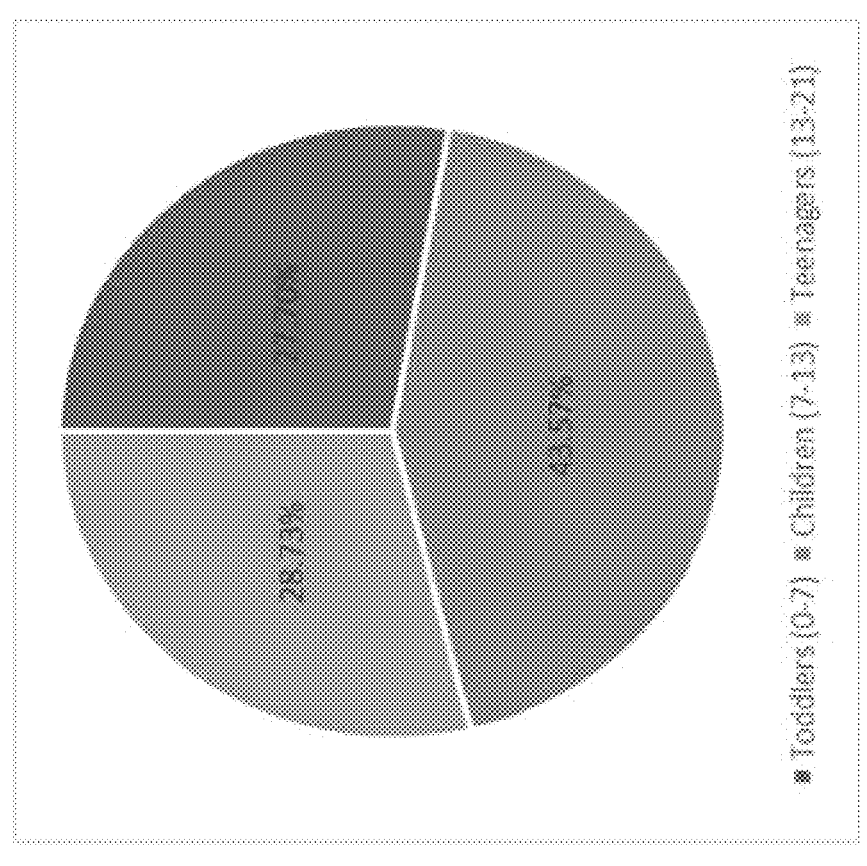
FIGS. 6A and 6B are graphs showing a distribution of a dataset used in an experiment to evaluate a performance of a machine learning model according to embodiments of the present disclosure.
Figure 6A:
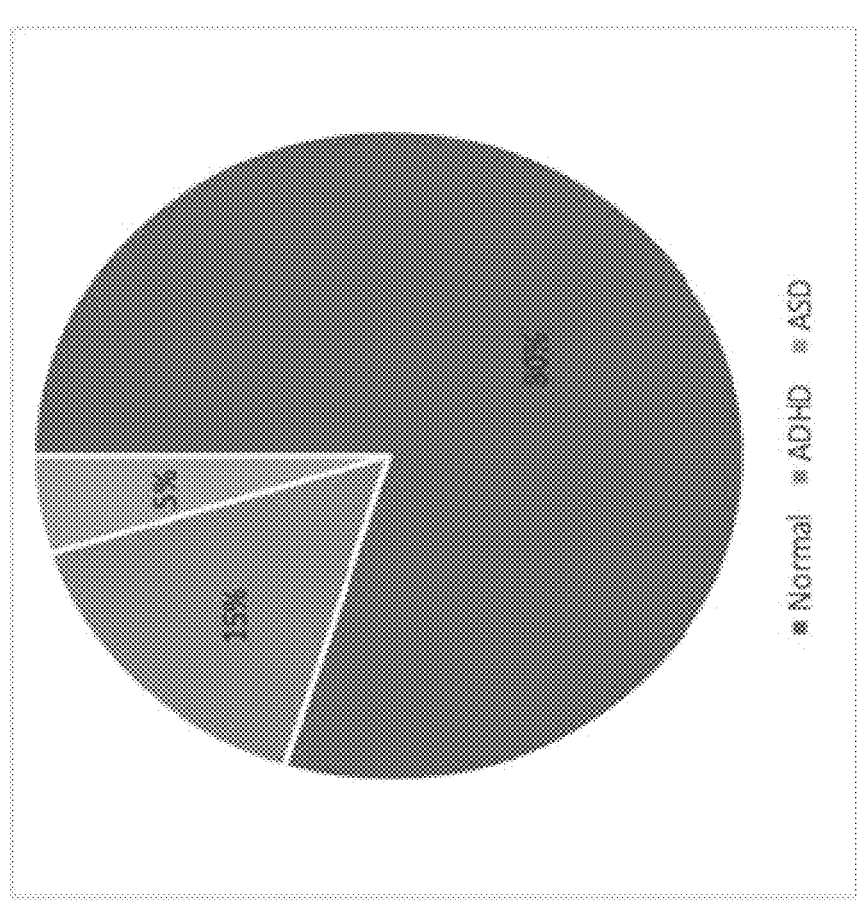

FIGS. 6A and 6B are graphs showing a distribution of a dataset used in an experiment to evaluate a performance of a machine learning model according to embodiments of the present disclosure.

Referring to FIGS. 6A and 6B, the dataset used in the experiment comprises a comprehensive collection of retinal samples obtained from a total of 6,146 patients. It includes a total of 412,559 retinal image samples labeled into three categories: Normal, ADHD, and ASD. The normal label contains 329,259 samples, constituting 79.81% of the total samples in the dataset. In the ADHD label, there are 63,250 samples, representing 15.33% of the total samples. Finally, ASD comprises 20,050 samples, making up 4.86% of the total samples.

The age groups are divided as follows. Age under 7: approximately 27.70% of the patients fall into this age category, reflecting a significant portion of the dataset. Age Between 7 and 13: A substantial 43.57% of the patients are within this age range and Age Between 13 and 21: the remaining 28.73% of patients.

In the experiment, to assess the effectiveness of the proposed method, it is conducted for a comprehensive series of experiments, which encompassed performance comparisons, the generation of confusion matrices and receiver operating characteristic curves, the exploration of various network architectures, and the application of data augmentation techniques. For the training and evaluation processes, a 5-fold cross-validation approach, a commonly used practice in machine learning research is employed. To ensure fairness and consistency in the comparison procedure, the identical training and testing procedures across all experiments are maintained.

FIG. 7 shows a table of performance comparison of overall ADHD classification results achieved by the computing device shown in FIG. 1 based on comparison with state-of the-art methods according to embodiments of the present disclosure.

The table 1 shown in FIG. 7 lists the performance comparison of the proposed method vs. well-known several approaches for ADHD classification. The well-known several approaches include architectures having networks such as VGG19, MobileNetV2, EfficientNet-B7, HRNet-32, and ResNet-50. Among these networks, VGG19, MobileNetV2, and EfficientNet-B7 displayed relatively poor results in the diagnosis of ADHD. This can be attributed to their relatively shallow convolutional layers, which hindered their ability to extract meaningful visual characteristics from the retinal fundus images. Conversely, HRNet-32 and ResNet-50, both equipped with deeper convolutional layers, exhibited slightly improved performance.

Ultimately, the proposed self-supervised-based method outperformed all the supervised-based comparison methods by a significant margin. This can be attributed to the self-supervised-based representation approach, which compelled the trained network to extract more robust and consistent features, ultimately leading to superior performance.

Figures 8A, 8B:
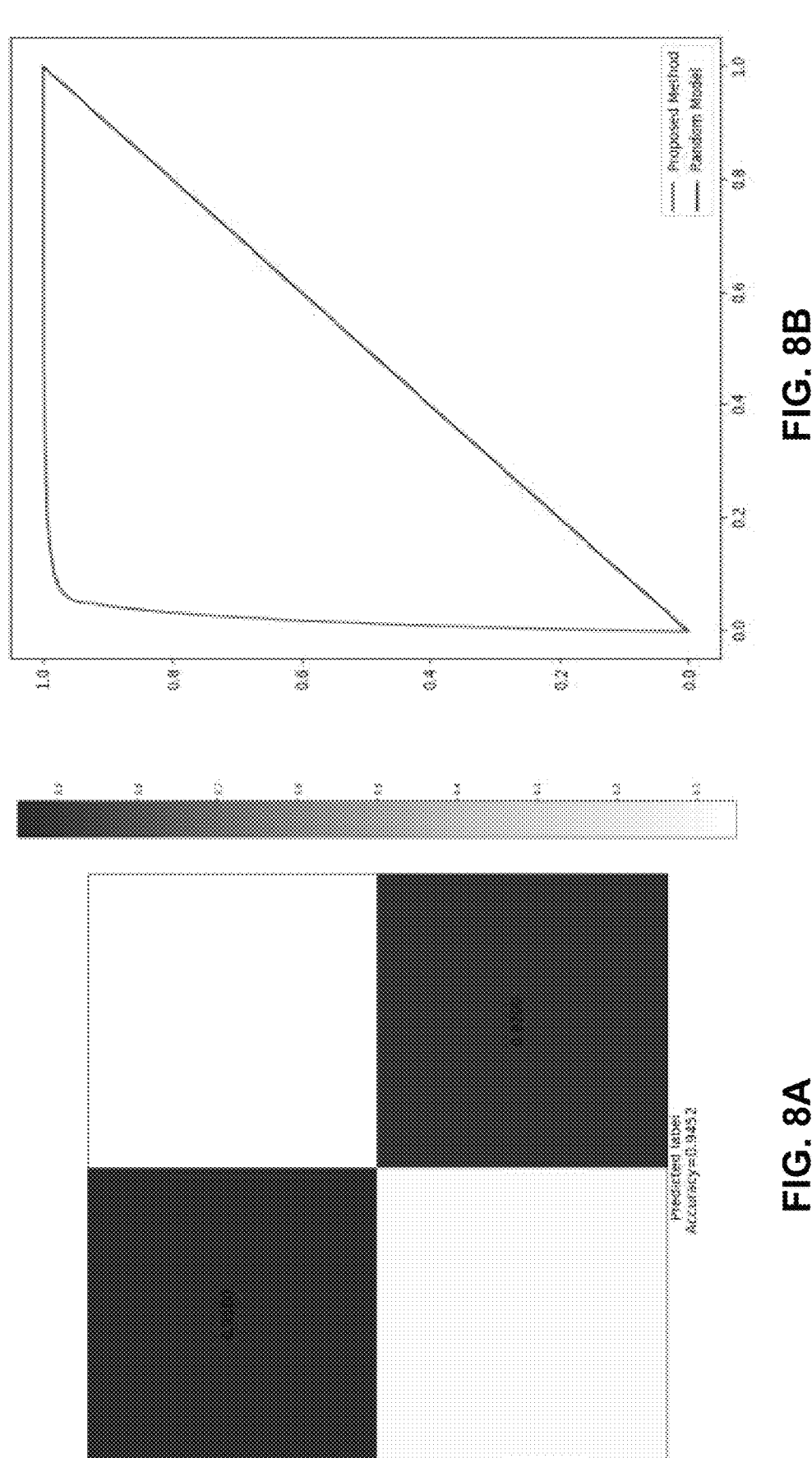
FIGS. 8A and 8B show a confusion matrix and a receiver operating characteristic curve of methods proposed by the computing device shown in FIG. 1 for ADHD classification according to embodiments of the present disclosure.

FIGS. 8A and 8B show a confusion matrix and a receiver operating characteristic curve of methods proposed by the computing device shown in FIG. 1 for ADHD classification according to embodiments of the present disclosure.

Referring to FIG. 8A, Examining the diagonal components of the confusion matrix provides a clear demonstration of the robustness and consistency achieved by the proposed method. Additionally, referring to FIG. 8B, the receiver operating characteristic curve assumes an almost rectangular shape in the upper-left corner, indicating that the proposed method exhibits exceptional discriminatory power and the ability to effectively distinguish between positive and negative cases.

FIG. 9 shows a table of performance comparison of overall ASD classification results achieved by the computing device shown in FIG. 1 based on comparison with state-of-the-art methods according to embodiments of the present disclosure.

The table 2 shown in FIG. 9 lists the performance comparison of the proposed method vs. well-known approaches detailed in FIG. 9 for ASD classification. Referring to the table 2, the shallow convolutional neural networks, specifically VGG19, MobileNet, and EfficientNet-B7, yielded poor results, while the deep networks showed slightly improved performance. Notably, the proposed method consistently outperformed all the compared methods, offering clear evidence of the effectiveness of the self-supervised representation learning approach in embodiments of the present disclosure.

Figures 10A, 10B:
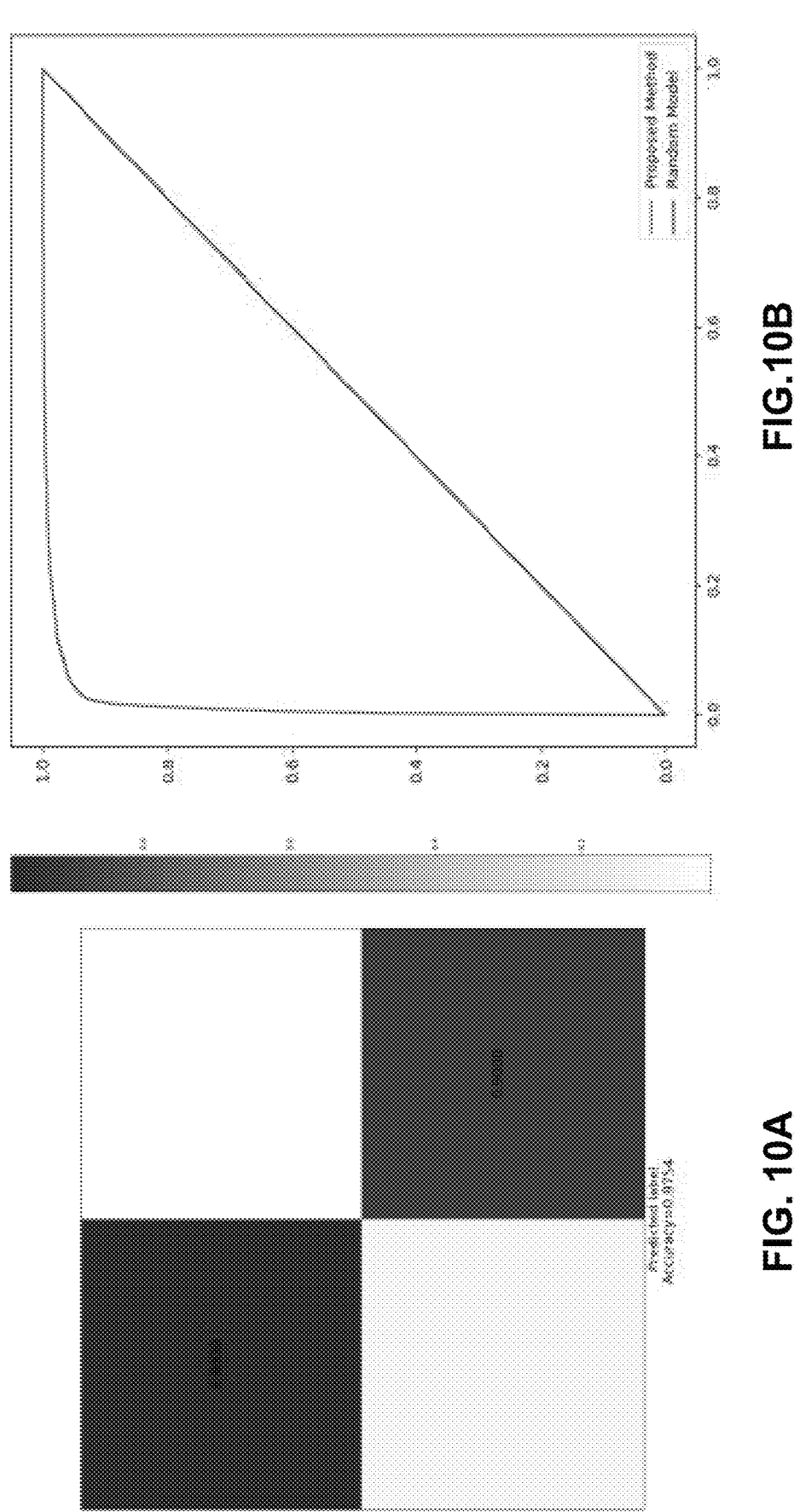
FIGS. 10A and 10B show a confusion matrix and a receiver operating characteristic curve of methods proposed by the computing device shown in FIG. 1 for ASD classification according to embodiments of the present disclosure.

FIGS. 10A and 10B show a confusion matrix and a receiver operating characteristic curve of methods proposed by the computing device shown in FIG. 1 for ASD classification according to embodiments of the present disclosure.

Referring to FIGS. 10A and 10B, the confusion matrix and the receiver operating characteristic curve for ASD classification have a similar trend compared to the ADHD classification. In the following chapters, we explain additional experiments in order to comprehensively examine the effectiveness of the proposed method from various perspectives.

FIG. 11 shows a table of data augmentation experiment achieved by the machine learning model of the computing device shown in FIG. 1 according to embodiments of the present disclosure.

The table 3 shown in FIG. 11 lists the data augmentation ways to enhance an accuracy of a machine learning model. In the table 3, the machine learning model is trained without any augmentation which serves as the baseline. Subsequently, the machine learning model is trained with four augmentation methods, including grayscale conversion, YCbCr color space transformation, sharpening, and histogram equalization. Each data augmentation method is then compared to the baseline to illustrate its impact on model performance.

Referring to the table 3, Grayscale, YCbCr, and sharpness augmentation did not lead to an increase in accuracy, whereas histogram equalization resulted in improved accuracy. This can be attributed to the fact that histogram equalization ensures a consistent pixel range distribution in the input retinal images, potentially enhancing the stability and accuracy of the inference process.

FIG. 12 is an exemplary flow diagram showing a training process of a machine learning model according to embodiments of present disclosure. The training process 1200 may be performed by a suitable machine learning model like a convolutional neural network.

At step S1210, the machine learning model receives a first fundus image and a second fundus image of human subject. In this case, the first and second fundus images is images diagnosed as having the neurodevelopmental disorder of a same category such as autism spectrum disorder (ASD) and attention-deficit/hyperactivity disorder (ADHD). At step S1220, the machine learning model may extract a first feature information and a second feature information from the first fundus image and a second fundus image, respectively. The first and second feature information may include various information such as a retinal vessel information and an optic nerve change information. Additionally, the machine learning models may use clinical information of the human subject. At step S1230, the machine learning model may extract a first embedding vector and a second embedding vector from the first fundus image and a second fundus image, respectively, based on the first and second feature information. In embodiments, the machine learning model may extract the first and second embedding vectors from the first and a second fundus image, respectively, regardless of the first and second feature information. At step S1240, the machine learning model may be repeatedly trained to maximize a similarity between the first embedding vector and the second embedding vector using various functions such as a cosine similarity function, a softmax function, a cross-entropy loss function.

Figure 13:
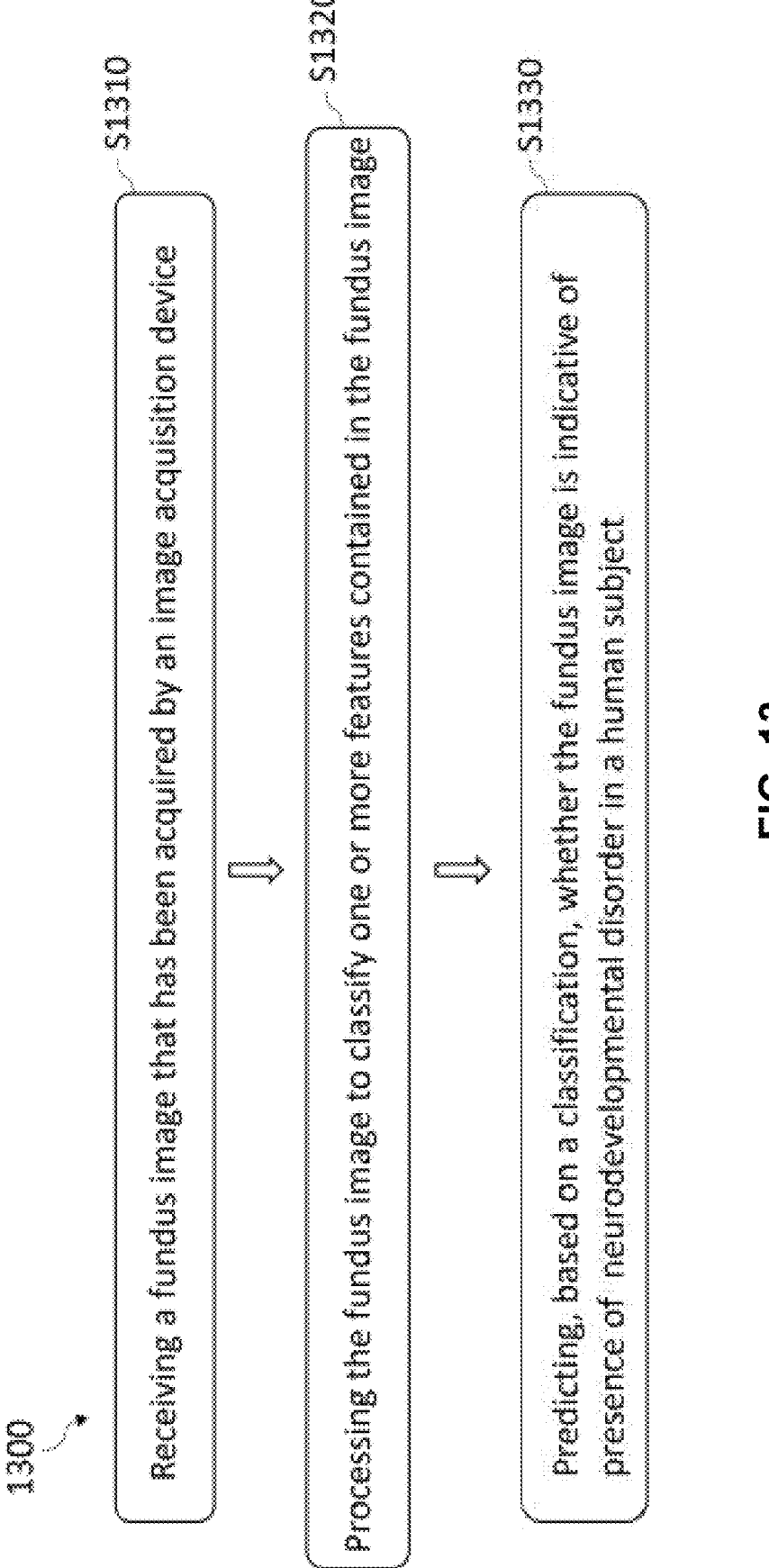
FIG. 13 is an exemplary flow diagram showing a prediction process of neurodevelopmental disorder using a fundus image according to embodiments of the present disclosure.

FIG. 13 is an exemplary flow diagram showing a prediction process of neurodevelopmental disorder using a fundus image according to embodiments of the present disclosure. The prediction process 1300 may be performed by a processor 111 installed into the computing device 110.

At step S1310, the processor 111 may receive a fundus image of human subject from an image acquisition device like a fundus camera. In embodiments, the fundus image may be stored in the memory unit 113, 313 or the storage device 115, 315 included to the computing device 110, 310 (as discussed in conjunction with FIGS. 1 and 2). At step S1320, the processor 111 may process the fundus image to classify one or more features contained in the fundus image. As the biometric information of the fundus image, the features or the feature information may be extract by a machine learning model 13, 33 installed into the processor 111. In embodiments, the feature information may be stored in the memory unit 113, 313 or the storage device 115, 315. At step S1330, the processor 111 may predict, based on a classification, whether the fundus image is indicative of presence of neurodevelopmental disorder such as autism spectrum disorder (ASD) and attention-deficit/hyperactivity disorder (ADHD) in a human subject.

Embodiments of the present disclosure may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hard-ware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a process-ing device. Examples of program modules include libraries, programs, routines, objects, components, and data struc-tures. In distributed computing environments, program mod-ules may be physically located in settings that are local, remote, or both.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present invention. It is intended that all permutations, enhancements, equivalents, combina-tions, and improvements thereto that are apparent to those skilled in the art upon a reading of the specification and a study of the drawings are included within the true spirit and scope of the present invention.

What is claimed is:

1. An apparatus for predicting of neurodevelopmental disorder using a fundus image of a subject, comprising:
    a processor; and
    a memory comprising one or more sequences of instruc-tions which, when executed by the processor, causes steps to be performed comprising:
    receiving the fundus image;
    processing the fundus image to classify one or more features contained in the fundus image using a machine learning model; and
    predicting, based on a classification, whether the fundus image is indicative of presence of neurodevelopmental disorder in the subject,
    wherein the machine learning model has been trained on stored fundus images obtained from at least two group of subjects who have previously been diagnosed as having the neurodevelopmental disorder, the machine learning model is trained by processes comprising;
    extracting a first embedding vector and a second embed-ding vector from a first fundus image and a second fundus image, respectively; and
    maximizing a similarity between the first embedding vector and the second embedding vector.

2. The apparatus of claim 1, wherein the first fundus image and the second fundus image are images diagnosed as having autism spectrum disorder or attention-deficit/hyper-activity disorder.

3. The apparatus of claim 1, wherein the processes further comprises extracting a first feature information and a second feature information from the first fundus image and the second fundus image, respectively.

4. The apparatus of claim 3, wherein the first feature information and the second feature information include at least one of retinal vessel information and optic nerve change information in the fundus image.

5. The apparatus of claim 1, wherein the similarity is calculated with a cosine similarity function.

6. An apparatus for predicting of neurodevelopmental disorder using a fundus image of a subject, comprising:
    a processor; and
    a memory comprising one or more sequences of instruc-tions which, when executed by the processor, causes steps to be performed comprising:
    receiving the fundus image;
    processing the fundus image to classify one or more features contained in the fundus image using a machine learning model; and
    predicting, based on a classification, whether the fundus image is indicative of presence of neurodevelopmental disorder in the subject,
    wherein the machine learning model has been trained on stored fundus images obtained from at least two group of subjects who have previously been diagnosed as having the neurodevelopmental disorder, the machine learning model is trained by processes comprising;
    extracting a first feature information and a second feature information from a first fundus image and a second fundus image, respectively;
    extracting a first embedding vector and a second embed-ding vector from the first fundus image and the second fundus image, respectively, based on the first feature information and the second feature information; and
    maximizing a similarity between the first embedding vector and the second embedding vector.

7. The apparatus of claim 6, wherein the first fundus image and the second fundus image are images diagnosed as having autism spectrum disorder or attention-deficit/hyper-activity disorder.

8. The apparatus of claim 6, wherein the first feature information and the second feature information include at least one of retinal vessel information and optic nerve change information in the fundus image.

9. A non-transitory computer-readable medium or media comprising one or more sequences of instructions which, when executed by a processor, causes steps for predicting of neurodevelopmental disorder using a fundus image of a subject, comprising:
    receiving the fundus image;
    processing the fundus image to classify one or more features contained in the fundus image using a machine learning model; and
    predicting, based on a classification, whether the fundus image is indicative of presence of neurodevelopmental disorder in the subject,
    wherein the machine learning model has been trained on stored fundus images obtained from at least two group of subjects who have previously been diagnosed as having the neurodevelopmental disorder, the machine learning model is trained by processes comprising;
    extracting a first embedding vector and a second embed-ding vector from a first fundus image and a second fundus image, respectively; and
    maximizing a similarity between the first embedding vector and the second embedding vector.

10. The non-transitory computer-readable medium or media of claim 9, wherein the processes further comprises extracting a first feature information and a second feature information from the first fundus image and the second fundus image, respectively.

* * * * *